United States Patent [19]

Kun et al.

[11] Patent Number: 5,262,564
[45] Date of Patent: Nov. 16, 1993

[54] SULFINIC ACID ADDUCTS OF ORGANO NITROSO COMPOUNDS USEFUL AS RETROVIRAL INACTIVATING AGENTS ANTI-RETROVIRAL AGENTS AND ANTI-TUMOR AGENTS

[75] Inventors: Ernest Kun, Mill Valley; Jerome Mendeleyev, San Francisco, both of Calif.

[73] Assignee: Octamer, Inc., Sausalito, Calif.

[21] Appl. No.: 969,874

[22] Filed: Oct. 30, 1992

[51] Int. Cl.$^5$ .................. C07C 311/31; A61K 31/095
[52] U.S. Cl. ...................................... 562/430; 564/98; 564/99
[58] Field of Search .................. 562/430; 564/98, 99; 514/562, 605

[56] References Cited

FOREIGN PATENT DOCUMENTS

| | | |
|---|---|---|
| 3-227923 | 1/1990 | Japan. |
| WO89/07441 | 8/1989 | PCT Int'l Appl. |
| WO89/07939 | 9/1989 | PCT Int'l Appl. |
| 2244646A | 11/1991 | United Kingdom. |

OTHER PUBLICATIONS

Umemoto et al.; Chem.-Biol Interact. (1988) 68(1-2), p. 57-69, Chem. Abstr. 110(15):130245.

Rice, W. et al., "Induction of endonuclease-mediated apoptosis in tumor cells by C-nitroso-substituted ligands of poly (ADP-ribose) polymerase." Proc. Natl. Acad. Sci. 89 7703-7707 (1992).

Buki, K. et al., "Destablization of Zn$^{2+}$ coordination in ADP-ribose transferase (polymerizing) by C-nitroso-1,2-benzopyrone coincidental with inactivation of the polymerase but not the DNA binding function." FEBS 290: 181-185 (1991).

Kirsten, E. et al., "Cellular regulation of ADP-ribosylation of proteins IV. Conversion of poly (ADP-Ribose) polymerase activity to NAD-glycohydrolase during retinoic acid-induced differentiation of HL60 cells." Experimental Cell Research 194:1-8 (1991).

Buki, K. et al., "Inhibitor binding of adenosine disphosphoribosyl transferase to the DNA primer site of reverse transcriptase templates." Biochem. Biophys. Res. Com. 180:496-503 (1991).

Cole, G. et al., "Inhibition of HIV-1 III-b replication in AA-2 and MT-2 cells in culture by two ligands of poly (ADP-ribose) polymerase: 6-amino-1,2 benzopyrone and 5-iodo-6-amino-1,2-benzopyrone." Biochem. Biophys. Res. Com. 180:504-514 (1991).

Henderson, L. et al., "Primary structure of the low molecular weight nucleic acid-binding proteins of murine leukemia viruses" J. Biol. Chem. 256(16) 8400-8403 (1981).

Gorelick, R. et al., "Point mutants of moloney murine leukemia virus that fail to package viral RNA: evidence for specific RNA recognition by a zinc-finger like protein sequence." Proc. Natl. Acad. Sci 85:8420-8424 (1988).

Gorelick, R. et al., "Noninfectious human immunodeficiency virus Type 1 mutants deficient in genomic RNA." J. Virol. 64:3207-3211 (1990).

Meric, C. et al., "Characterization of moloney murine leukemia virus mutants with single amino acid substitutions in the Cys-His box of the nucleocapsid protein." J. Virol. 63:1558-1568 (1989).

Aldovini, A. et al., "Mutations of RNA and protein (List continued on next page.)

*Primary Examiner*—Marianne M. Cintins
*Assistant Examiner*—Michael B. Hydorn
*Attorney, Agent, or Firm*—Albert P. Halluin

[57] ABSTRACT

The subject invention provides for novel anti-tumor and anti-retroviral compounds. More specifically, the invention relates to the sulfinic acid adducts of therapeutic C-nitroso compounds. The formation of the adducts increases the stability and more solubility of the C-nitroso compounds. These compounds include the L-cysteinesulfinic acid adducts of 6-nitroso-1,2-benzopyrone and 3-nitrosobenzamide. The invention also provides for compositions containing one or more of the compounds, and for methods of treating retroviral infections, cancer, infectious virus concentration with the subject compounds and compositions.

2 Claims, 3 Drawing Sheets

OTHER PUBLICATIONS sequences involved in human immunodeficiency virus Type I packaging result in production of noninfectious virus." J. Virol 64:1920–1926 (1990).

Lever, A. et al., "Identification of a sequence required for efficient packaging of human immunodeficiency virus Type I RNA into virions." J. Virol 63:4085–4087 (1989).

Gradwohl, G. et al., "The second zinc-finger domain of poly (ADP-ribose) polymerase determines specificity for single-stranded breaks in DNA." Proc. Natl. Acad. Sci. 87 2990–2994 (1990).

South, T. et al., "113 Cd NMR studies of 1:1 Cd adduct with an 18-residue finger peptide from HIV-1 nucleic acid binding protein, p. 7." J. Am. Chem. Soc. 111 395-396 (1989).

South, T. et al., "Zinc fingers and molecular recognition. Structure and nucleic acid binding studies of an HIV zinc fingerlike domain." Biochem. Pharm. 40:123–129 (1990).

Summers, M. et al., "High-resolution structure of an HIV zinc fingerlike domain via a new NMR-based distance geometry approach." Biochemistry 29:329–340 (1990).

Yamagoe, S. et al., "Poly (ADP-ribose) polymerase inhibitors suppress UV-induced human immunodeficiency virus type 1 gene expression at the posttranscriptional level." Molecular and Cellular Biology 11(7) 3522–3527 (1991).

Krasil'Nikov, I. et al., "Inhibitors of ADP-ribosylation as antiviral drugs: Experimental study of the model of HIV infection." VOPR.VIRUSOL (Russia) 36(3) 216–218 (1991).

Furlini, G. et al., "Increased poly (ADP-ribose) polymerase activity in cells infected by human immunodeficiency virus type-1." Microbiologica 14(2) 141–148 (1991).

Ibne-Rasa, K. et al., "O-Nitrosobenzamide. A possible intermediate in the von Richter reaction." J. Org. Chem. 28(11) 3240–3241 (1963).

Seidel, W. et al., "Oxidation of aromatic hydrazides." Chemical Abstracts 82 82 Col. 16505X (1975).

Wubbels, G. et al., "Mechanism of water-catalyzed photo-isomerization of p-nitrobenzaldehyde." J. Org. Chem 47(24) 4664–4670 (1982).

Bamberger, E. et al., "Ueber die Einwirk von p-Toluolsufinsaure auf nitrosobenzo." Chem. Ber. 34:228–241 (1901).

Belayev, E. et al., "Reactions of Nitrosobenzenes With Sulfur-Containing Compounds." Khim. Texhnol. Polim. 4:60–65 (1975).

Darchen, A. et al., "Arenesulphinic Acids. Nitroso Protecting Reagents Applicable to some nitrosoarenes." J.C.S. Chem. Commun. 820 (1976).

Wajer, A. et al., "C–Nitroso compounds. Part XVI. The reaction of C–nitroso compounds with benzenesulfinic acid. An ESR study of alkyl and aryl benzenesulfonyl nitroxides." Rec. Trav. Chim. 89:696–704 (1970).

Sestilli, P. et al., "Analogues of benzamide as poly (ADP-ribose) transferase inhibitors: a study on structure acivity relationships." Pharm. Res. Commun. 20:613–614 (1988).

Cardellini, L. et al., "Fenton's reagent in dimethyl sulforide: an unusual sulphonylating system. X-Ray crystallographic analysis of 4–N,N–dimethylamino-N,-N-dimethanesulphonylaniline." J. Chem. Soc. Perkins Trans 2:1929–1934 (1990).

Kovacic, P. et al., "Reduction potentials in relation to physiological activities of benzenoid and heterocyclic nitroso compounds: comparison with the nitro precursors." Bioorganic Chemistry 18: 265–275 (1990).

Elhardt, W. J. et al., "Nitrosoimidazoles: highly bactericidal analogues of 5-nitroimidazole drugs." J. Med. Chem. 31: 323–329 (1988).

McClelland, R. A. et al., "Products of the reductions of 2-nitroimidizoles." J. Am. Chem. Soc. 109: 4308–4314 (1987).

Noss, M. B. et al., "Preparation, toxicity and mutagenicity of 1-methyl-2-nitrosoimidazole." Biochem. Pharm. 37: 2585–2593 (1988).

Varghese, A. J. et al., "Modification of guanine derivatives by reduced 2-nitroimidazoles." Cancer Research 43: 78–82 (1983).

Buki, K. et al., "Destabilization of Zn(II) coordination in poly(ADP-Ribose) polymerase by 6-nitroso-1,-2-benzopyrone coincidental with inactivation of the polymerase but not with the DNA binding function." The Paul Mandel International Meeting of Poly(ADP-Ribosyl)ation Reactions. Abstract 22C May 30, 1991.

Mulcahy, R. T. et al., "Cytotoxicity and glutathione depletioni by I-methyl-2-nitrosoimidazole in human colon cancer cells." Biochem. Pharm. 38: 1667–1671 (1989).

Noss, M. B. et al., "I-Methyl-2-nitrosoimidazole: cytotoxic and glutathione depleting capabilities." Int. J. Radiation Oncology Biol. Phys. 16: 1015–1019 (1989).

SULFINIC ACID ADDUCTS OF ORGANO NITROSO COMPOUNDS USEFUL AS RETROVIRAL INACTIVATING AGENTS ANTI-RETROVIRAL AGENTS AND ANTI-TUMOR AGENTS

Cross Reference to Related Applications

This application is related to copending applications Ser. No. 07/780,809 filed Oct. 22, 1991 and Ser. No. 07/893,429 filed Jun. 4, 1992, the disclosures of which are incorporated herein by reference.

BACKGROUND OF THE INVENTION

1. Field of the Invention

The present invention relates generally to the field of retroviral therapeutic agents and their use in treating retroviral infections and cancers. More specifically it relates to those therapeutic aromatic C-nitroso compounds which destabilize zinc fingers.

2. Description of the Prior Art

The enzyme ADP-ribose transferase (ADPRT) (E.C.4.2.30) is a chromatin.bound enzyme located in the nucleus of most eukaryotic cells. The enzyme catalyzes the polymerization of the ADP-ribose moiety of nicotinamide adenine dinucleotide (NAD+) to form poly (ADP-ribose). The polymer is covalently attached to various nuclear proteins, including the polymerase itself.

The many varied roles that ADP-ribosylation plays in cellular metabolism have made ADPRT a target for drugs essentially useful for combating neoplasia and viral infections. Numerous physiological activities have been detected for compounds that inhibit the polymerase activity of ADPRT. Such activities include a cell cycle dependent prevention of carcinogen-induced malignant transformation of human fibroblasts (Kun, E., Kirsten, E., Milo, G. E. Kurian, P. and Kumari, H. L. (1983) *Proc. Natl. Acad. Sci. USA* 80:7219-7223), conferring also carcinogen resistance (Milo, G. E., Kurian, P., Kirsten, E. and Kun, E. (1985) *FEBS Lett.* 179:332-336), inhibition of malignant transformation in hamster embryo and mouse C3H10T1/2 cell cultures (Borek, C., Morgan, W. F., Ong, A. and Cleaver, J. E. (1984) *Proc. Natl. Acad. Sci. USA* 81 243-247), deletion of transfected oncogenes from NIH 3T3 cells (Nakayashu, M., Shima, H., Aonuma, S., Nakagama, H., Nagao. M. and Sugimara, T. (1988) *Proc. Natl. Acad. Sci. USA* 85:9066-9070), suppression of the mitogenic stimulation of tumor promoters (Roman, F., Menapace, L. and Armato, V. (1983) *Carcinogenesis* 9:2147-2154), inhibition of illegitimate DNA recombinations (Waldman, B. C. and Waldman, A. (1990) *Nucl. Acids Res.* 18:5981-5988) and integration (Farzaneh, F., Panayotou, G. N., Bowler, L. D., Hardas, B. D., Broom, T., Walther, C. and Shall, S. (1988) *Nucl. Acids Res.* 16: 1139-11326), induction of sister chromatid exchange (Ikushima, T. (1990) *Chromosoma* 99:360-364) and the loss of certain amplified oncogenes (Grosso, L. E. and Pitot, H. C. (1984) *Biochem. Biophys. Res. Commun.* 119:473-480; Shima, H., Nakayasu, M., Aonums, S., Sugimura, T. and Nagao, M. (1989) *Proc. Natl. Acad. Sci. USA* 86:7442-7445).

Compounds known to inhibit ADPRT polymerase activity include benzamide (Kun, E., Kirsten, E., Milo, G. E. Kurian, P. and Kumari, H. L. (1983) *Proc. Natl. Acad. Sci. USA* 80:7219-7223), substituted benzamides (Borek, C., Morgan, W. F., Ong, A. and Cleaver, J. E. (1984) *Proc. Natl. Acad. Sci. USA* 81:243-247; Romano, F., Menapace, L. and Armato, V. (1983) *Carcinogenesis* 9; 2147-2154; Farzaneh, F., Panayotou, G. N., Bowler, L. D., Hardas, B. D., Broom, T., Walther, C. and Shall, S. (1988) *Nucl. Acids Res.* 16:11319-11326.; Grosso, L. E. and Pitot, H. C. (1984) *Biochem. Biophys. Res. Commun.* 119:473-480; Shima, H., Nakayasu, M., Aonums, S., Sugimura, T. and Nagao, M. (1989) *Proc. Natl Acad. Sci. USA* 86:7442-7445), 3-aminonaphthylhydrazide (Waldman, B. C. and Waldman, A. (1990) *Nucl. Acids Res.* 18:5981-5988), isoquinoline, quercetin, and coumarin (1,2-benzopyrone) (Milo, G. E., Kurian, P., Kirsten, E. and Kun, E. (1985) *FEBS Lett.* 179: 332-336). The antitransforming and anti-neoplastic effect of 1,2 benzopyrone were demonstrated in vitro and in vivo (Tseng, et al., (1987) *Proc. Natl. Acad. Sci. USA* 84:1107-1111).

The 6-nitroso-benzopyrones were only recently discovered (U.S. patent application No. 07/412,783). The only remotely related compounds found in the literature are 6-nitro-1,2-benzopyrone and 6-amino-1,2-benzopyrone (6-ABP) (*J. Pharm. Soc. Jap.*, 498:615 (1923)) for which, only scarce medicinal evaluation has been reported. In particular, testing was done for sedative and hypnotic effects (*J. Pharm. Soc. Japan.* 73:351(1953); Ibid. 74:271(1954)), hypothermal action (Yakuoaku Zasshi. 78:491 (1958)), and antipyretic, hypnotic, hypotensive and adrenolytic action (Ibid. 83:1124 (1963)). No significant application for any of these compounds has been described except for 6-ABP.

2-nitrosobenzamide (Irne-Rasa, K. M. and Koubek, E. (1963) *J. Org. Chem.* 28:3240-3241), and 4-nitrosobenzamide (Wubbels, G. G., Kalhorn, T. F., Johnson, D. E. and Campbell, D. (1982) *J. Org. Chem.* 47:4664-4670), have been reported in the chemical literature, but no medical or therapeutic use of these isomers is known. Neither of these articles suggest the use of nitrosobenzamides as ADPRT inhibitors or for use as anti-retroviral agents or 10 anti-cancer agents.

The anti-viral and anti-tumorigenic actions of substituted and unsubstituted 6-amino-1,2-benzopyrone and 5-iodo-6-amino-1,2-benzopyrone is the subject of copending U.S. patent applications Ser. No 585,231 filed on Sep. 21, 1990 entitled "6-Amino-1,2-Benzopyrones Useful for Treatment of Viral Diseases" and Ser. No. 600,593 filed on Oct. 19, 1990 entitled "Novel 5-Iodo-6-Amino-1,2-Benzopyrones and Their Metabolites Useful as Cytostatic and Antiviral Agents", which are incorporated herein by reference.

The precursor molecule, 1,2-benzopyrone (coumarin), was shown to be an inhibitory ligand of adenosinediphosphoribosyl transferase (ADPRT), a DNA-binding nuclear protein present in all mammalian cells (Tseng, et al, (1987) *Proc. Nat. Acad. Sci. USA.* 84:1107-1111).

Hakam, et al., *FEBS Lett.*, 212:73 (1987) has shown that 6-amino-1,2-benzopyrone (6-ABP) binds specifically to ADRPT at the site that also binds to DNA, indicating that both 6-ABP and DNA compete for the same site on ADPRT. Synthetic ligands of ADPRT inhibit DNA proliferation, particularly in tumorigenic cells, (Kirsten, et al., (1991) *Exp. Cell. Res.* 193:1-4). These ligands have been found to inhibit viral replication and are the subject of the copending U.S. patent application entitled "6-Amino-1,2-Benzopyrones useful for Treatment of Viral Diseases," Ser. No. 585,231, filed on Sep. 21, 1990 which is hereby incorporated by reference.

Retroviral nucleocapsid (NC) proteins and their respective gag precursors from all strains of known retroviruses contain at least one copy of a zinc-binding polypeptide sequence of the type Cys-$X_2$-Cys-$X_4$-His-$X_4$-Cys (CCHC) (Henderson, et al., *Biol. Chem.* 256:8400–8406 (1981)), i.e., a zinc finger domain. This CCHC sequence is essential for maintaining viral infectivity (Gorelick, et al., *Proc. Natl. Acad. Sci. USA* 85:8420–8424 (1988), Gorelick, et al., *J. Virol.* 64:3207–3211(1990)), therefore, it represents an attractive target for viral chemotherapy. The HIV-1 gag proteins function by specifically binding to the HIV-1 RNA, anchoring it to the cell membrane for budding or viral particles (Meric, , et al., *J. Virol.* 63: 1558–1658 (1989) Gorelick, et al., *Proc. Natl. Acad. Sci. USA* 85:8420–8424 (1988), Aldovini, et al., *J. Virol.* 64:1920–1926 (1990), Lever, et al, *J. Virol.* 63:4085–4087 (1989)). Site-directed mutagenesis studies demonstrated that modification of Cys or His residues results in defective viral RNA packaging and noninfectious viral particles are formed (Aldovini et al., *J. Virol.* 64:1920–1926 (1990), Lever, et al, *J. Virol.* 63:4085–4087 (1989)). The highly abundant nonhistone nuclear protein of eukaryotes, poly(ADP-ribose) polymerase (E.C.2.4.4.30). also contains two CCHC-type zinc fingers located in the basic terminal polypeptide domain, as analyzed by site directed mutagenesis (Gradwohl, et al., *Proc. Natl. Sci. USA* 87:2990–2992 (1990)).

In copending U.S. Ser. No. 07/893,429 filed Jun. 4, 1992 the disclosure of which is incorporated herein by reference, it is shown that 3-nitrosobenzamide and 6-nitroso-1,2-benzopyrone inhibit propagation of HIV-1 in human lymphocytes and also eject zinc from isolated HIV-1 NC fingers.

Recently published experiments have shown that aromatic C-nitroso ligands of poly (ADP-ribose) polymerase preferentially destabilize one of the two zinc fingers coincidental with a loss of enzymatic activity but not DNA binding capacity of the enzyme protein (Buki, et al., *FEBS Lett.* 290:181–185 (1991)). Based on the similarity to results obtained by site-directed mutagenesis (Gradwohl, et al, *Proc. Natl. Sci. USA* 87:2990–2992 (1990)), it appears that the primary attack of C-nitroso ligands occurred at zinc finger FI (Buki, et al., *FEBS Lett.* 290:181–185 (1991)). 6-nitroso-1,2-benzopyrone (6-NOBP) and 3-nitrosobenzamide (3-NOBA), two C-nitroso compounds that inactivate ADPRT at one zinc finger site completely suppressed the proliferation of leukemic and other malignant human cells and subsequently produced cell death. Tumoricidal concentrations of the drugs were relatively harmless to normal bone marrow progenitor cells and to superoxide formation by neutrophil granulocytes. The cellular mechanisms elicited by the C-nitroso compounds consists of apoptosis due to DNA degradation by the nuclear calcium/magnesium dependent endonuclease (Rice et al. *Proc. Natl. Sci. USA* (1992) 89:7703–7707. This endonuclease is maintained in a latent form by poly(ADP-ribosyl)ation, but inactivation of ADPRT by C-nitroso drugs depresses the DNA-degrading activity.

While these nitroso compounds have been found to be quite effective in preliminary tests, they are relatively water insoluble at physiological pH, exhibit limited stability and limited predictability of delivery to the affected cells due to their solubility and stability characteristics. Thus it is of interest to construct C-nitroso compounds, especially the aromatic C-nitroso compounds, in a more stable and more water soluble form for convenient use as anti-retroviral and anti-cancer compositions.

The chemical reaction of an aromatic sulfinic acid (p-tolunesulrinic acid) with an Ar—N=O (nitrosobenzene) is known (*Chemische Berichte.* 34: 228–241 (1901). The preparation and use of aromatic sulfinic acids (specifically benzenesulfinic acid and p-toluenesulfinic acid) as chemical protecting groups for certain Ar—N=O compounds (e.g., p-PhC(O)—$C_6H_4$— N=O) for purposes of electrochemical synthesis has been reported *J. C. S. Chem Commun.*, 820 (1976). The method was developed for trapping and protecting nitroso compounds generated during electrochemical synthesis. No suggestion was made that these compounds could be used as drugs.

The preparation of adducts of alkyl—N=O compounds with aryl sulfinic acids (*Rec.Trav.Chim.* 89:696–704 (1970) has been reported as well as the reaction of simple alkyl sulfinic acids with Ar—N=O compounds (Chem. Abstr. 89:189390s (1977). The use a sulfinic acid derivative of the amino acid (L-cysteine-sulfinic acid, denoted as L-alanine,2-sulfino in Chemical Abstracts) has not been reported, however.

SUMMARY OF THE INVENTION

This invention concerns a new class of compounds comprising adducts of aliphatic sulfinic acids of anti-cancer and anti-retroviral C-nitroso compounds. The adducts prepared by the invention are more stable and more water soluble at physiological pH's than the uncoupled C-nitroso compounds. In addition to incurring little or no toxicity by use in living organisms, the adducts offer facile deprotection (activation) of the C-nitroso compounds upon transfer to neutral or alkaline media, especially in physiological media.

DESCRIPTION OF THE PREFERRED EMBODIMENTS

Definitions

Figure 1A:
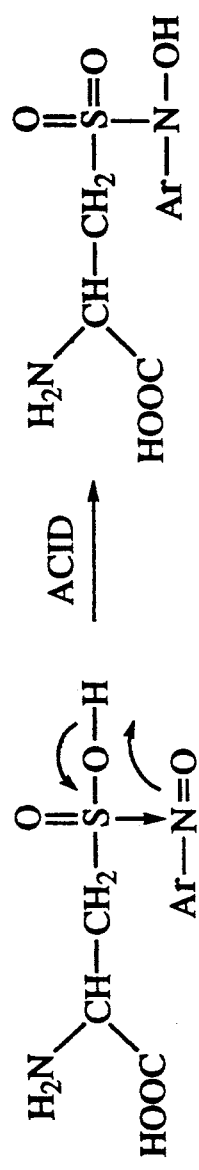
FIG. 1A shows the proposed mechanism for the reaction of aromatic C-nitroso compounds (Ar—N=O) with L-cysteine sulfinic acid to give the adducts (N-substituted aryl hydroxylamines).
Figure 1B:
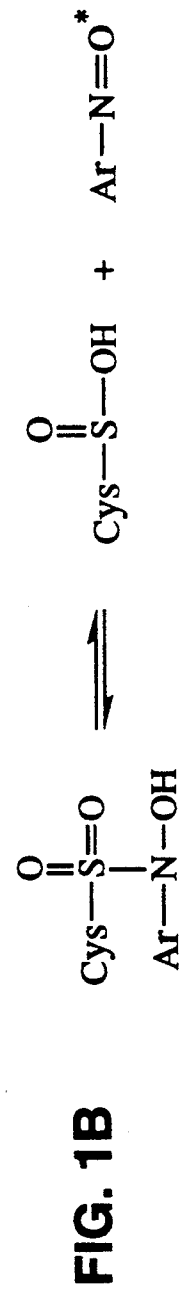
FIG. 1B snows the proposed mechanism for the reaction of the N-substituted aryl hydroxylamines in neutral media. The adducts are in equilibria with the free nitroso compounds and L-cysteinesulfinic acid, i.e., the adducts dissociate to their constituents.
Figure 1C:
FIG. 1C shows the proposed mechanism for the reaction of the N-substituted aryl hydroxylamines in basic media. The reaction is shifted far to the right.

The term "biological material" refers to any biological material extracted from a living organism, including blood, plasma, cerebrospinal fluid, organs, and the like, as well as the processed products of biological material extracted from a living organism.

The term "biological composition" as used herein, refers to a composition comprising a biological material and a compound of interest.

The term "cancer" as used herein refers to malignant tumors consisting of cells that defy not simply the normal controls on their proliferation, but also the normal controls on their position.

The term "retrovirus" as used herein refers to RNA viruses which utilize the enzyme reverse transcriptase to transcribe infecting RNA chains into DNA complements.

The term "nitroso compound" refers to compounds having the formula:

wherein $R_2$ is an aliphatic, aromatic or aryl aliphatic moiety having 1 to 36 carbon atoms, preferably 6 to 24 carbon atoms and most preferably 7 to 14 carbon atoms. This moiety may be substituted with one or more substitutes such as halogens, amines, carboxy groups, etc.

Sulfinic acids refer to compounds having the formula:

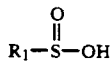

wherein $R_1$ is a substituted or unsubstituted aliphatic moiety having 1 to 24 carbon atoms, preferably 2 to 6 carbon atoms and more preferably 3 to 4 carbon atoms.

Adducts of nitroso compounds refer to compounds of the following formula:

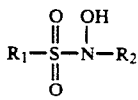

wherein $R_1$ is a substituted or unsubstituted aliphatic moiety having 1 to 24 carbon atoms, preferably 2 to 6 carbon atoms and more preferably 3 to 4 carbon atoms and $R_2$ is an aliphatic, aromatic or aryl aliphatic moiety having 1 to 36 carbon atoms, preferably 6 to 24 carbon atoms and most preferably 7 to 14 carbon atoms. This moiety may be substituted with one or more substituents such as halogens, amines etc.

$R_1$ is preferably:

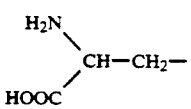

$R_2$ is preferably the residue of:

3-nitrosobenzamide:

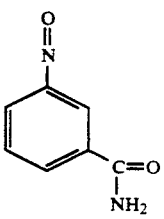

6-nitroso-1,2-benzopyrone:

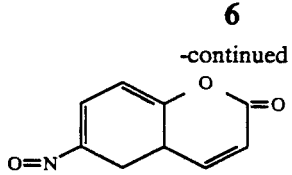

Preferred adducts of the invention include, for example:

N-(3-carbamoylbenzene)-N-hydroxy-L-cysteinesulfonamide:

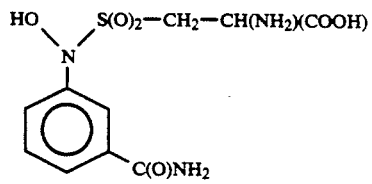

N-(6-[1,2-benzopyrone]-N-hydroxy-L-cysteinesulfonamide:

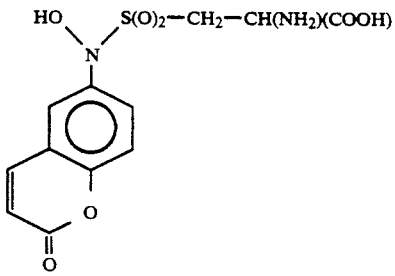

DETAILED DESCRIPTION OF THE INVENTION

Methods of Preparation

Detailed synthesis of 6-nitro-1,2-benzopyrone, 3-nitro-benzamide, 5-nitro-1(2H)-isoquinolinone, 7-nitroso-1(2H)-isoquinolinone, is described in pending U.S. Ser. Nos. 07/780,809, filed Oct. 22, 1991 and 07/893,429, filed Jun. 4, 1992 which are hereby incorporated by reference as well as PCT/US91/08902, filed Nov. 26, 1991.

Detailed synthesis of 3-nitrosoenzamide and the sulfinic acid derivatives of 3-nitroxobenzamide and 6-nitroso-1,2-benzopyrone are provided in the example section below.

3-nitrosobenzamide is prepared by oxidizing 3-aminobenzamide with 3-chloroperoxybenzoic acid in a relatively concentrated solution in dimethyl formamide. The reaction mixture is quenched by pouring it into aqueous sodium carbonate, whereby 3-nitrosobenzamide precipitates while 3-chlorobenzoic acid remains in solution. The product, 3-nitrosobenzamice, is collected by filtration and then purified by recrystalization from 50% aqueous acetic acid.

The sulfinic acid derivatives of 3-nitrosobenzamide and 6-nitroso-1,2-benzopyrone are prepared by reacting commercial L-cysteinesulfinic acid hydrate with the nitroso compounds under acidic conditions. The mixtures are chilled to about −20° C. for up to 24 h and then filtered to remove any azoxy side-product precipitate. The filtrate is rotarily evaporated and then precipitated by addition of ethanol to obtain the sulfinic acid adducts in dried form.

Another aspect of the subject invention is providing for the increased stability of the sulfinic acid adducts in the solid state and increased solubility in aqueous solutions, compared to the uncoupled forms of the C-nitroso compounds.

An additional aspect of the invention is the facile de-protection (activation) of the compounds to the free nitroso form upon administration into neutral or slightly basic media.

Pharmaceutical Formulations

In practice, the compounds of this invention, and any of their pharmaceutically acceptable salts, may be administered in amounts, either alone or in combination with each other, and in the pharmaceutical form which will be sufficient and effective to inhibit neoplastic growth or viral replication or prevent the development of the cancerous growth or viral infection in the mammalian host.

Administration of the active compounds and salts described herein can be via any of the accepted modes of administration for therapeutic agents. These methods include systemic or local administration such as oral, parenteral, transdermal, subcutaneous, or topical administration modes. The preferred method of administration of these drugs is intravenous, except in those cases where the subject has topical tumors or lesions, where the topical administration may be proper. In other instances, it may be necessary to administer the composition in other parenteral or even oral forms.

Depending on the intended mode, the compositions may be in the solid, semi-solid or liquid dosage form, such as, for example, injectables, tablets, suppositories, pills, time-release capsules, powders, liquids, suspensions, or the like, preferably in unit dosages. The compositions will include an effective amount of the compound, or pharmaceutically acceptable salt thereof, and in addition it may include any conventional pharmaceutical excipients and other medicinal or pharmaceutical drugs or agents, carriers, adjuvants, diluents, etc., as customary in the pharmaceutical sciences.

For solid compositions, in addition to the compounds, such excipients as, for example, pharmaceutical grades of mannitol, lactose, starch, magnesium stearate, sodium saccharin, talcum, cellulose, glucose, sucrose, magnesium carbonate, and the like may be used. The compounds of the subject invention may be also formulated as suppositories using, for example, polyalkylene glycols, for example, propylene glycol, as the carrier.

Liquid, particularly injectable compositions can, for example be prepared by dissolving, dispersing, etc. the compound in a pharmaceutical solution such as, for example, water, saline, aqueous dextrose, glycerol, ethanol, DMSO and the like, to thereby form the injectable solution or suspension.

If desired, the pharmaceutical composition to be administered may also contain minor amounts of nontoxic auxiliary substances such as wetting or emulsifying agents, pH buffering agents, and other substances such as, for example, sodium acetate, triethanolamine oleate, etc.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

A more recently devised approach for parenteral administration employs the implantation of a slow. release or sustained-release systems, which assures that a constant level of dosage is maintained, see U.S. Pat. No. 3,710,795, which is incorporated herein by reference.

Any of the above pharmaceutical compositions may contain 0.01–99%, preferably 1–70% of the active ingredient.

Actual methods of preparing such dosage forms are known, or will be apparent to those skilled in this art, and are described in detail in *Remington's Pharmaceutical Sciences*, Mack Publishing Company, Easton, Pa., 17th Edition, 1985. The composition or formulation to be administered will, in any event, contain such quantity of the active compound(s) that will assure that a therapeutically effective amount will be delivered to a patient. A therapeutically effective amount means an amount effective to prevent development of or to alleviate the existing symptoms of the subject being treated.

The amount of active compound administered will, of course, be dependent on the subject being treated, on the subject's weight, the severity of the affliction, the manner of administration and the judgment of the prescribing physician. However, an effective dosage may be in the range of 1 to 12 mg/kg/day, preferably 1 to 5 mg/kg/day, given only for 1–2 days at one treatment cycle. Generally, the upper limit for the drug dose determination is its efficacy balanced with its possible toxicity.

Application

The subject invention provides for methods of reducing the titer of infectious viruses, particularly retroviruses (including the retrovirus HIV-1) in biological materials by inactivating the viruses. Viruses may be inactivated by contact between the compound of interest and the virus. The term "reducing" includes the complete elimination of all the infectious viruses of interest, as well as a diminution in the titer of the infectious viruses. It is of particular interest to reduce the number of infectious viruses in biological material that is to be introduced into a living organism so as to reduce the possibility for infection. It is also of interest to reduce the titer infectious viruses that might be present in or on non-biological materials that come into contact with living organisms, such non-biological materials include surgical instruments, dental instruments, hypodermic needles, public sanitary facilities, and the like.

A preferred embodiment of the subject invention is the reduction in infectious virus concentration in blood.

Although the effective amount of the viral-inactivating compound used in the subject method will vary in accordance with the nature of the compound and the particular material, biological or otherwise of interest, a preferred concentration of N-(3-carbamoylbenzene) N-hydroxy-L-cysteinesulfonamide or N-(6-[1,2-benzopyrone]-N-hydroxy-L-cysteinesulfonamide is about 15 micromolar. An effective amount may readily be determined by testing the effect of a range of concentrations of the compound of interest on the viral titer of a composition containing a virus of interest.

The subject methods of reducing infectious virus concentration in biological materials inactivate viruses by employing the step of adding an effective amount of the compounds.

Another aspect of the invention is to provide for novel compositions consisting of biological materials containing an effective amount of the adducts. Preferred compounds include N-(3-carbamoylbenzene)-N-hydroxy-L-cysteinesulfonamide and N-(6-[1,2-benzopyrone]-N-hydroxy-L-cysteinesulfonamide. The subject biological compositions may have diminished viral concentrations and may thus be administered with less risk of infection than comparable biological materials.

The invention having been described, the following examples are offered to illustrate the subject invention by way of illustration, not by way of limitation.

Examples

I. Preparation of 3-nitrosobenzamide (3-NOBA)

3-Aminobenzamide (5.0 g.) is dissolved in N,N-dimethylformamide (DMF) solvent (25 ml) and then chilled in an ice bath. 3-Chloroperoxybenzoic acid (2.1 equivalents) is also dissolved in DMF solvent (25 ml) in a 250-ml flask equipped with a stirrer and thermometer and, as needed, an ice bath. This solution is chilled to 0°-5° C., the ice bath is removed, and to it, with stirring, is added all at once the chilled 3-aminobenzamide solution. The mixture immediately becomes a transparent brown color, but within 0.5 minutes turns to a deep green, and within 1.0 minutes the temperature rises to 70° C., at which time the ice bath is reapplied to the reaction flask whereupon the temperature begins to fall, and is allowed to fall to 25° C., and stirring is continued for a total of 5 minutes. Some precipitation occurs (3,3'-azoxybenzamide side-product), thereafter the mixture is chilled to 5° C. for 10 minutes. The chilled mixture is filtered (suction) to remove the azoxy precipitate, and the green filtrate is poured into chilled (5°-10° C.) and stirred aqueous 0.40M $Na_2CO_3$ (200 ml), resulting in a light green suspension, and the suspension is stirred for an additional 10 minutes at 5°-10° C. to assure maximal product precipitation. Note that the pH of the suspension is about 8.5, which assures that 3-chlorobenzoic acid is retained in the aqueous solution as the sodium salt. The precipitate is then collected on a section funnel and rinsed with deionized water (100 ml). This material, which is 3-NOBA (mostly as the tan dimer) containing residual 3,3'-azoxybenzamide side-product impurity, is then transferred, while damp, to a suitable flask and to it is added 50% aqueous acetic acid (200 ml). The mixture is warmed to 65°-70° C. to dissolve the dimer into the soluble monomeric 3-NOBA (green) and stirred for 5 minutes at 65° C. The azoxy impurity (yellow) is poorly soluble and remains undissolved. The warm mixture is filtered (gravity) to give a clear green filtrate, which is allowed to cool. It is then chilled and placed in the refrigerator freezer (−20° C.) overnight to allow the 3-NOBA to redeposit as the light tan solid dimer. On the following day the solid product is collected on a suction filter, rinsed with fresh solvent, and the product cake is then dried by vacuum under mild warming for several hours. One typically obtains 2.24 g of dry 3-NOBA containing a trace of the azoxy impurity. The product is recrystallized by dissolving it again in 50% aqueous acetic acid (120 ml) and allowing to redeposit overnight in the freezer. After collection, rinsing and drying in vacuo. the weight is 2.08 g. (37% overall yield). TLC shows the material is 3-NOBA with a trace of the azoxy impurity.

II. Synthesis and Characterization of N-(L-cysteinsulfonyl)aryl hvdroxylamines.

An example of a method for the preparation of N-(L-cysteinesulfonyl) aryl hydroxylamine is provided as follows.

A solution cf 3-nitrosobenzamide (3-NOBA), 6-nitroso-1,2-benzopyrone (6-NOBP), 4-nitrosobenzamide (4-NOBA) or nitrosobenzamide (NOPH) in glacial acetic acid (15 ml) is prepared in a 50-ml flask by warming to completely dissolve the compound. After cooling to room temperature, a solution of L-cysteinesulfinic acid hydrate (3.0 mMoles) in distilled water (7.5 ml) at room temperature is added with magnetic stirring. The addition is in sequential 1-ml portions by pipet until fully added (about ½ min). As the addition progresses the characteristic green color of Ar—N=O fades and finally the solution is usually a pale yellow. After stirring at ambient temperature for 20 min the solution is chilled in the freezer(−20 C.) for up to 24 hours, to remove the often-encountered azoxy impurity in nitroso compounds, which come out of solution as a yellow precipitate owing to poor solubility in aqueous solvents. The chilled solution is then filtered (suction) to remove the precipitate, and then the clear filtrate is transferred to a rotary evaporation flask and under reduced pressure most of the acetic acid and water is removed, leaving a concentrated solution of the product in the form of a semi-viscous liquid. To this liquid is added 25 mL of absolute ethanol, whereupon the adduct precipitates as a white solid. After mixing and dispersing the precipitate in the ethanol with a spatula, the mixture is chilled in the freezer and then the precipitate is collected on a suction funnel, rinsed with the absolute ethanol, and then dried by vacuum pumping. This precipitated form of the product, when dry, is in the form of a white or tan powder, and the yield is typically 70–80%. The material can be recrystallized from the water, aqueous ethanol, or 1M formic acid. With respect to melting points, all of the compounds prepared thus far display decomposition melting points above 100 degrees C. A proposed mechanism for the reaction of aromatic C-nitroso compounds with L-cysteine sulfinic acids is shown in FIG. 1A. The proposed mechanism for the reactions of the N-substituted aryl hydroxylamines in neutral (FIG. 1B) and basic (FIG. 1C) are also shown.

Mass Spectrometry of Reaction Products

The reaction products were analyzed by high resolution mass spectrometry. Mass spectrum: (FAB+mode, m/z)

N-benzene-N-hydroxy-L-cysteinesulfonamide (NOPH adduct):

for MH+, calculated for $C_9H_{13}N_2O_5S$: 261.054519 found: 261.054290 (dev 0.9 ppm)

N-(3-carbamoylbenzene)-N-hydroxy-L-cysteinesulfonamide (3-NOBA Adduct):

for MH+, calculated for $C_{10}H_{13}N_2O_7S$: 329.044348 found: 304.060010 (dev 1.1 ppm)

N-(6-[1,2-benzopyrone}-N-hydroxy-L-cysteinesulfonamide (6-NOBP adduct):

for MH+, calculated for $C_{12}H_{13}N_2O_7S$; 329.044348 found: 329.044330 (dev. 0.1 ppm N-(4-carbamoylbenzene)-N-hydroxy-L-cysteinesulfonamide (4-NOBA adduct:

for MH+, calculated for $C_{10}H_{14}N_3O_6S$:304.060322 found: 304.059710 (dev 2.0 ppm)

Specific Analysis of N-(3-carbamoylbenzene)-N-hydroxy-L-cysteinesulfonamide (3-NOBA adduct):

HPLC Analysis:

A sample of the 3-NOBA adduct powder was dissolved in potassium phosphate buffer (100 mM phosphate, pH 4.2) at a concentration of 20 mM. A 10 ul aliquot of the solution was injected into the HPLC. HPLC was performed with the following instrumental components: Waters Association (Milford, Mass., USA) Model 6001 solvent delivery pumps, Waters Model 680 gradient controller, Waters Model 730 data module, and Hewlett-Packard (Santa Clara, Calif., USA) Model 1040A high speed spectrophotometric detector. Chromatographic data were stored in a Hewlett-Packard Model 9121D disc memory system and plotted by a Hewlett Packard 747A graphic plotter.

Figure 2:
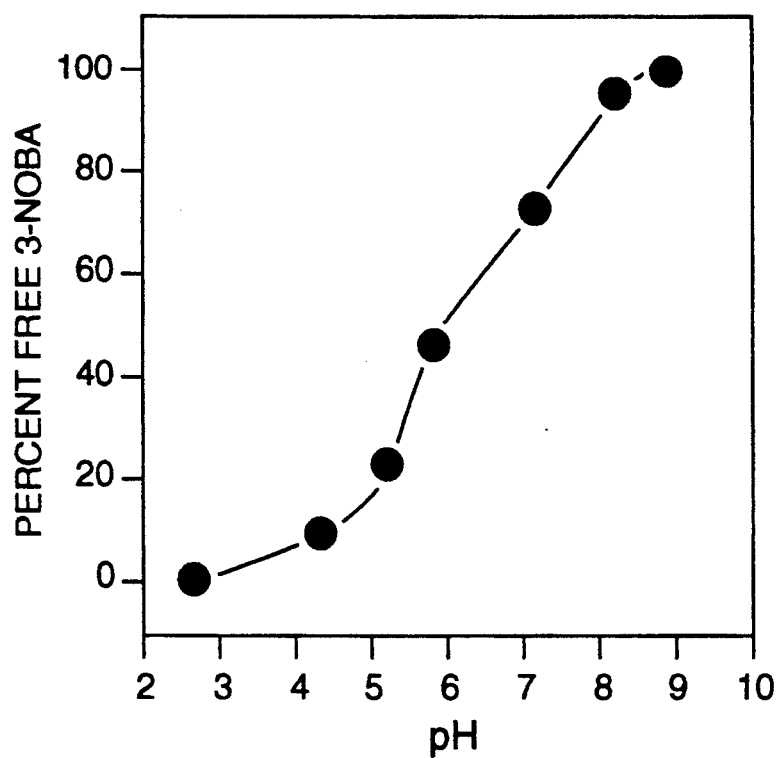
FIG. 2 shows the percentage of free 3-NOBA released by its adduct at various pH's, determined spectrophotometrically.

The HPLC column was a Beckman-Altex (Berkeley, Calif. USA) analytical reversed-phase column (Ultrasphere ODS, 5 um, 25 cm×4.6 mm I.D.), with a precoloumn packed with the same sorbent as the analytical column. Chromatography was carried out at ambient temperature. The HPLC flow rate was 1.2 ml/min with the UV detector set at 260 nm. A ternary solvent system using linear gradients was employed: Solvent A: 0.05 M potassium phosphate, pH 6.8; Solution B: 0.05 M potassium phosphate, pH 6.8+30% methanol and solution C: 50% water, 50% acetonitrile (v/v). Upon sample injection the gradient started from 100% A to 100% B in 30 minutes, immediately followed by the gradient from 100% B to 50%/50% C in 15 minutes followed by the gradient from 50% B/%0% C to 100% C in 3 minutes, ending by pumping 100% C for 5 minutes. Results are shown in FIG. 2.

UV Absorption Spectrum

3-NOBA-Cy adduct, measured in a $1 \times 10^{-4}$ M solution in potassium phosphate buffer (100 mM, pH 4.2), $\lambda_{max}$(E): 273nm ($4.70 \times 10^3$) and 250 nm ($4.54 \times 10^3$)

pH Titration

Figure 3:
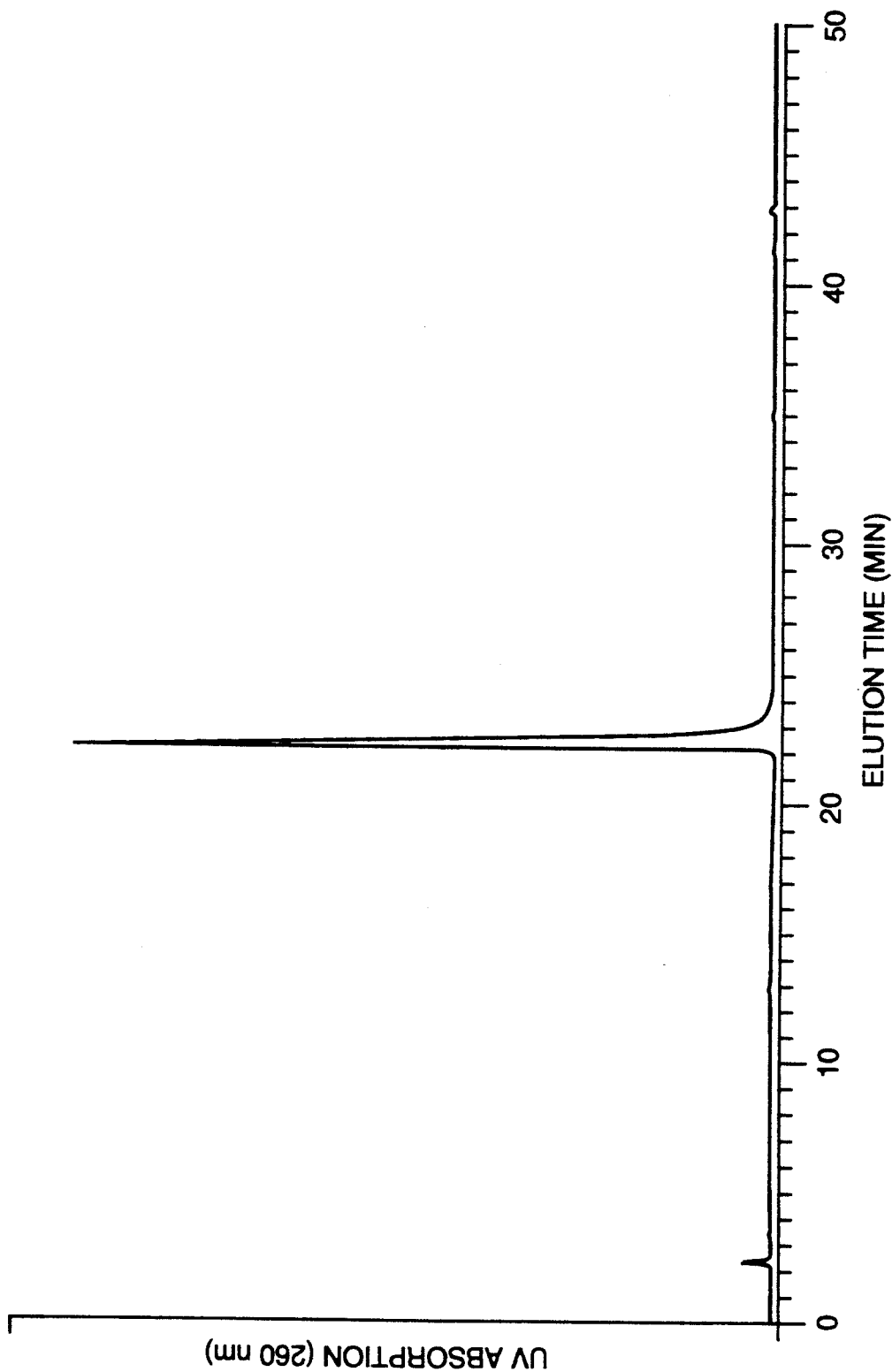
FIG. 3 shows the HPLC chromatogram of the adduct of 3-NOBA with L-cysteinesulfinic acid.

FIG. 2 shows the percent of 3-NOBA in the free nitroso form in aqueous solution as a function of pH. Solutions having an initial 20 mM concentration of 3-NOBA-Cy adduct (pH 2.69) were treated with various amounts of concentrated NaOH solution, the pH measured with a miroelectrode and $A_{725}$ determined in a UV-VIS spectrometer. At a pH below 3, the solution is colorless. At pH greater than 9 a yellow color interferes with measurement of the green free nitroso compound. Results are shown in FIG. 3.

III. Similarity of the Effects of 3-Nitroso Benzamide (NOBA) and its Cysteine Sulfinic Acid Adduct (NOBA-Cy) on DNA Unwinding in 855-2 Cells and in U-937 cells 855-2B-lymphocyte precursor leukemia cells (*Science* 249, 178-181, 1990) or U-937 histiocytic lymphoma cells (*Int. J. Cancer* 17, 565-577, 1976) were seeded at a cell density of $0.2 \times 10^2$ ml and incubated for 18 hours in the presence of the indicated drug concentrations; the fluorescence assay for DNA unwinding was carried out as described (Cancer Res. 41, 1889-1892, 1981).

| Cell line/treatment | % double stranded DNA | % Unwinding |
|---|---|---|
| A. 855-2 cells | | |
| Control (no drug) | 99 ± 1.0 | |
| NOBA 15 μM | 74 ± 3.5 | 25 ± 3.5 |
| NOBA 30 μM | 41 ± 2.5 | 58 ± 2.5 |
| NOBA-Cy 15 μM | 73 ± 3.0 | 26 ± 3.0 |
| NOBA-Cy 30 μM | 40 ± 3.5 | 59 ± 3.5 |
| B. U-937 cells | | |
| Control (no drug) | 97 ± 1.5 | |
| NOBA 60 μM | 51 ± 4.5 | 46 ± 4.5 |
| NOBA-Cy 60 μM | 42 ± 4.0 | 55 ± 4.0 |

NOBA-: 3-nitrosobenzamide
NOBA-Cy: N-(3-carbamoylbenzene)-N-hydroxy-L-cysteinesulfonamide NOBA was added from a 40 mM stock solution in dimethyl formamide and NOBA-Cy from a 40 mM stock solution in 100 mM glycine buffer, ph 6.0, containing 10% propylene glycol, to give the indicated final concentrations.

IV. Effects on Cell Replication and Apoptosis in 855-2Cells on 2NOBA, 3-NOBA, 4-NOBA, and the 3-NOBA-Cysteine Sulfinic Acid Adduct (3-NOBA-Cy)

855-2 cells were seeded at a density of $0.2 \times 10^6$ cells/ml; drugs were added from 40 mM stock solutions at the time of seeding and the effects were assessed by counting the total cell numbers and the numbers of trypan blue positive cells after 18 hours of incubation in culture medium at 37° C.

| Drug added | cell number ($\times 10^6$/ml) | % dead cells |
|---|---|---|
| Control (no drug) | 0.4 | |
| 2-NOBA 20 μM | 0.22 | 30 |
| 2-NOBA 40 μM | 0.19 | 62 |
| 3-NOBA 20 μM | 0.20 | 28 |
| 3-NOBA 40 μM | 0.18 | 65 |
| 4-NOBA 20 μM | 0.25 | 18 |
| 4-NOBA 40 μM | 0.21 | 78 |
| 3-NOBA-Cy 20 μM | 0.20 | 25 |
| 3-NOBA-Cy 40 μM | 0.18 | 66 |

2-NOBA: 2-nitrosobenzamide
3-NOBA: 3-nitrosobenzamide
4-NOBA: 4-nitrosobenzamide
3-NOBA-Cy: N-(3-carbamoylbenzene)-N-hydroxy-L-cysteinesulfonamide The error range of cell counting was ±10 to 15%.

Additional Examples

In a similar manner as shown in Examples II other nitroso compounds are reacted with sulfinic acids to form sulfinic acid derivatives. Representative examples include:

| Nitroso Compound | Sulfinic Acid | Adduct |
|---|---|---|
| 3-NOBA | hydroxymethanesulfinic acid | N-(3-carbamoylbenzene)-N-hydroxy-hydroxymethanesulfonamide |
| 6-NOBP | hydroxymethanesulfinic acid | N(6-[1,2-benzopyrone]-N-hydroxy-hydroxymethanesulfonamide |
| 3-NOBA | 2-aminoethanesulfinic acid | N-(3-carbamoylbenzene)-N-hydroxy-2-aminocthanesulfonamide |
| 6-NOBP | 2-aminoethanesulfinic acid | N(6-[1,2-benzopyrone]-N-hydroxy-2-aminocthanesulfonamide |
| 3-NOBA | 3-aminopropanesulfinic acid | N-(3-carbamoylbenzene)-N-hydroxy-3-aminopropanesulfonamide |
| 6-NOBP | 3-aminopropanesulfinic acid | N(6-[1,2-benzopyrone]-N-hydroxy-3-aminopropanesulfonamide |
| 3-NOBA | phenylmethanesulfinic acid | N-(3-carbamoylbenzene)-N-hydroxy-phenylmethanesulfonamide |

-continued

| Nitroso Compound | Sulfinic Acid | Adduct |
|---|---|---|
| 6-NOBP | phenylmethanesulfinic acid | N(6-[1,2-benzopyrone]-N-hydroxy-phenylmethanesulfonamide |
| 3-NOBA | 4-hydroxybenzenesulfinic acid | N-(3-carbamoylbenzene)-N-hydroxy-4-hydroxybenzenesulfonamide |
| 6-NOBP | 4-hydroxybenzenesulfinic acid | N(6-[1,2-benzopyrone]-N-hydroxy-4-hydroxybenzenesulfonamide |
| 3-NOBA | 4-carboxylbenzesulfinic acid | N-(3-carbamoylbenzene)-N-hydroxy-4-carboxylbenzenesulfonamide |
| 6-NOBP | 4-carboxylbenzesulfinic acid | N(6-[1,2-benzopyrone]-N-hydroxy-4-carboxylbenzenesulfonamide |
| 3-NOVA | 4-methoxybenzenesulfinic acid | N-(3-carbamoylbenzene)-N-hydroxy-4-methoxybenzenesulfonamide |
| 6-NOBP | 4-methoxybenzenesulfinic acid | N(6-[1,2-benzopyrone]-N-hydroxy-4-methoxybenzenesulfonamide |

The adducts listed above are suitable for use as anti-cancer and anti-retrovirus agents in a manner analogous to the previously described adducts.

All publications, patents, and patent applications cited above are herein incorporated by reference.

The foregoing written specification is considered to be sufficient to enable one skilled in the art to practice the invention. Indeed, various modifications of the above-described modes for carrying out the invention which are obvious to those skilled in the field of pharmaceutical formulation or related fields are intended to be within the scope of the following claims.

We claim:

1. A compound having the following structural formula:

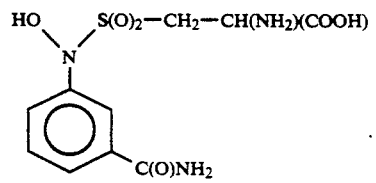

2. A pharmaceutical formulation comprising a compound having the chemical formula:

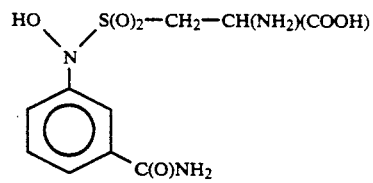

and a pharmaceutical excipient.

* * * * *